United States Patent [19]

Short et al.

[11] 4,072,535
[45] Feb. 7, 1978

[54] PRECOMPACTED-STARCH BINDER-DISINTEGRANT-FILLER MATERIAL FOR DIRECT COMPRESSION TABLETS AND DRY DOSAGE CAPSULES

[75] Inventors: Rolland W. P. Short; Frank Verbanac, both of Decatur, Ill.

[73] Assignee: A. E. Staley Manufacturing Company, Decatur, Ill.

[21] Appl. No.: 617,133

[22] Filed: Sept. 26, 1975

Related U.S. Application Data

[60] Continuation-in-part of Ser. No. 102,033, Dec. 28, 1970, abandoned, which is a division of Ser. No. 839,590, July 7, 1969, Pat. No. 3,622,677, which is a continuation-in-part of Ser. No. 646,496, June 16, 1967, abandoned.

[51] Int. Cl.² ............................................. C08L 3/02
[52] U.S. Cl. ...................................... 106/210; 127/32
[58] Field of Search ........................... 106/210; 127/32

[56] References Cited

U.S. PATENT DOCUMENTS

| | | | |
|---|---|---|---|
| 2,098,293 | 11/1937 | Jefferies | 127/32 |
| 2,168,524 | 8/1939 | Horesi | 127/32 |
| 2,845,367 | 7/1958 | Alt et al. | 127/32 |
| 3,119,719 | 1/1964 | Kott et al. | 127/32 |
| 3,137,592 | 6/1964 | Protzman et al. | 127/32 |
| 3,171,747 | 3/1965 | Kessinger | 99/93 |
| 3,196,044 | 7/1965 | Kott | 127/33 |
| 3,399,081 | 8/1968 | Bernetti | 127/71 |
| 3,622,677 | 11/1971 | Short | 424/361 |

OTHER PUBLICATIONS

Chem. Abst. 54:23,184.

Primary Examiner—Theodore Morris
Attorney, Agent, or Firm—Howard J. Barnett; Charles J. Meyerson

[57] ABSTRACT

A free-flowing binder-disintegrant powder material consisting essentially of a precompacted-starch powder, especially adapted for use in direct compression tabletting machines to produce non-friable tablets having excellent disintegration properties. This precompacted-starch powder is also useful as a free-flowing filler for blending with dry powder ingredients in dry-dosage capsules. The precompacted-starch powder is obtained by subjecting an ungelatinized granular starch to physical compaction without supplementary thermal energy, but with sufficient mechanical energy input to obtain a precompacted-starch having birefringent granules and non-birefringent fragments of granules and some aggregates of granules and fragments, and then dried to a moisture content of 9–16% total weight basis. After precompacting, the starch is pulverized to form a free-flowing powder having a loose bulk density of 0.5 to about 0.7 grams per milliliter. The precompacted-starch powder is essentially free of +40 mesh particles, at least 90% of the particles are −80 mesh, at least about 10% is +270 mesh, and from about 30% to 90% is −270 mesh size on a total weight basis (U.S. Standard Sieve Series, A.S.T.M. Specifications).

Cold water solubility of the precompacted-starch powder is in the range of from 4% to about 40% by weight, preferably about 10% to 20% by weight, and this powder is capable of being formed into a hard, non-friable tablet in combination with other active ingredients in a direct compression tabletting machine, the precompacted-starch powder being dually functional as both a binder and disintegrant. The resulting tablet has a hardness index of at least about 4 kilograms, preferably at least 8 kilograms, a friability loss of less than 1% by weight, a swelling power of 2.5 to about 12, preferably at least 8, and is capable of effectively disintegrating when placed in water.

11 Claims, 4 Drawing Figures

PRECOMPACTED-STARCH BINDER-DISINTEGRANT-FILLER MATERIAL FOR DIRECT COMPRESSION TABLETS AND DRY DOSAGE CAPSULES

CROSS-REFERENCE

This application is a continuation-in-part of U.S. application Ser. No. 102,033, filed Dec. 28, 1970 now abandoned, which is a division of U.S. application Ser. No. 839,590, filed July 7, 1969, now U.S. Pat. No. 3,622,677, which was a continuation-in-part of U.S. application Ser. No. 646,496, filed June 16, 1967, now abandoned.

BACKGROUND OF THE INVENTION

Many nutritive, pharmaceutical and chemical materials are dispensed in convenient tablet or capsule form. In many cases, the amount of active ingredient required to accomplish a desired therapeutic, nutritive or chemical effect is very small. Inert diluents, fillers, binders, excipients and disintegrants, therefore, become very important in determining the practicality and convenience of making tablets or capsules to administer such active ingredients effectively.

There are a number of methods for making tablets. One of the most direct and efficient methods is by "direct compression tabletting." However, the direct compression tabletting apparatus requires a free-flowing powder material which completely and rapidly fills the mold prior to the application of compression. The free-flowing powder must also contain the desired amount of active ingredients to insure efficacy of the tablet for the intended purpose. This latter requirement is especially important in pharmaceutical tablets where too much active ingredient may be just as serious as too little.

The properties needed for a desirable carrier material include: flowability and correct particle size to facilitate accurate blending, and to facilitate correct and rapid loading of the direct compression tabletting apparatus; binding ability and bulk density to facilitate obtaining a tablet of sufficient hardness, substantially no friability, but which will readily disintegrate when ingested, or when put into use by otherwise subjecting it to moisture. Examples of such uses include aspirin tablets, including "Chewable" tablets, food additive tablets, plant fertilizer tablets, vitamin tablets, dry detergent tablets, animal feed medications and water treatment tablets. For certain specific purposes, such as efficacy tests, it may be desirable to administer "placebo" tablets containing no active ingredient, but otherwise indistinguishable from other tablets containing an active ingredient.

Some materials fill all the requirements for making a hard, non-friable tablet, but fail when the tablet is to be used. The carrier material in some cases does not aid in the disintegration of the tablet, and may actually prevent it. Fully gelatinized starch, which is considered 100% cold water soluble, behaves in the latter way. The outer surface of tablets made from fully gelatinized starch "gels" rapidly on contact with water. The tablet becomes "gummy" and never dissolves or disintegrates completely. Even a blend or mixture of fully gelatinized starch with granular starch does not dissolve effectively when tabletted. The completely cold water soluble, gelatinized portion of the blend tends to gel as indicated above, and it interferes with the disintegration of the remaining portion of the tablet.

Of the multitude of forms in which pharmaceutical products may be dispensed, the compressed tablet form is, by far, the most frequently employed today. Ease of packaging and handling, and, most important, accuracy of dosage in administration are among the advantages stemming from the use of medicament-containing tablets. For essentially the same reasons, the compressed tablet also plays an important role in other fields such as a dispensing unit. Examples of non-pharmaceutical materials marketed in compressed tablet form include such diverse materials as laundry detergents, confections, artificial sweeteners, fish foods, plant growth regulators, pesticides, herbicides, and dyes. While the actual characteristics of various tablets differ depending on the particular nature and planned use of the several tablets, the generally more important characteristics fall into three areas of consideration.

Since most tablets are designed for use in accurately dispensing an active material into a fluid medium, an evaluation of the tablet includes a consideration of the tablet disintegration properties in the fluid medium. While some tablets, such as those designed for use as a throat lozenge, desirably are slowly disintegrative in the fluid medium in which they are placed for use, in most cases rapid disintegration of the tablet is desired. For example, a tablet embodying an ingestible analgesic, such as aspirin, should rapidly break down in the digestive fluid of the stomach to make the active ingredient promptly available to the organism.

The second and third important tablet characteristics, friability and hardness, are somewhat related in that as tablet hardness increases the friability of the tablet generally decreases. Excessive friability is undesirable, since dusting and crumbling of the tablet results in at least some diminution in active ingredient dosage, detracts from the tablet appearance and consumer appeal, and reduces the effectiveness of any tablet markings. Insufficiently hard tablets, in addition to exhibiting the effects of excessive friability, are prone to breakage and chipping, particularly in transport where they may be subjected to repeated mechanical shock.

Accordingly, for most purposes, and particularly for pharmaceutical application, a hard, non-friable tablet possessing acceptable disintegration characteristics is the goal of the tablet manufacturer. Other properties are, of course, important such as color stability and non-hygroscopicity, but the main criteria for a tabletting material is that it be freely flowable to load the tabletting machine, that it compress well to form a hard non-friable tablet, and that the resulting tablet disintegrate effectively when used.

Certain materials such as sodium chloride, paradichlorobenzene, hexamethylenetetramine, and certain medicaments are readily directly compressed alone in dry form into a firm, coherent mass in a tablet machine. However, the majority of active ingredients in order to be tabletted require a binding agent to be added. The tabletted formulations generally also contain additional ingredients, such as lubricants, disintegrants, fillers, glidants, colorants, and the like. The term "binding agent," "binder," and "filler" are self-explanatory. A disintegrant is an agent which is effective, when the tablet is placed in the proper fluid environment, to promote destruction of the tablet's physical integrity. A typical disintegrant employed in tabletting is granular starch, however, granular starch is not freely flowable and will not form a hard, non-friable tablet in direct compression tabletting apparatus. A given material may perform more than one of the single functions of binding, filling, and promoting disintegration. The goal of the tablet making is to find a material which performs as many of these functions as possible.

In general, three methods are known for the preparation of mixtures suitable to be employed in a tablet-making machine. In two of the methods commonly used for the preparation of tabletting machine feed material, the goal in each is the preparation of the feed material in the form of a free-flowing powder. One technique involves a dry, and the other a wet, method of granulation. Dry granulation is also referred to as "slugging" or "double compression." In accordance with the slugging technique, the initially prepared pulverulent admixture of active ingredient, filler, binder and the like is formed into large tablets or slugs by dry compression molding. These slugs are then milled to granules of predetermined size adapted to be used as the feed to the tablet-making machine. This method is expensive, requiring considerable equipment, labor and power. The technique, moreover, does not always provide suitable tablets.

The wet granulation technique involves adding a moistening agent such as water or ethylene glycol to the tabletting ingredient mixture to prepare a moistened mass, oven drying the wetted mass, and milling the dried mass into granules adapted to be used in the tabletting machine. The wet granulation method likewise is undesirably time-consuming and expensive. This method, moreover, has the limitation of not being useful when the tablet ingredients are incompatible to wetting or are heat-sensitive.

The third and simplest procedure employed in preparing tabletting formulations involves intimately and uniformly dry blending the ingredients employed, e.g., active ingredient, binder, filler, disintegrant, and lubricants, to provide a pulverulent powder mixture displaying the requisite flowability for adequate feeding to the direct compression tablet machine. Since in this method the granulation step is eliminated, the formulations are said to be "directly compressible" into tablets, and the tablet-forming operation is referred to as "direct-compression" tabletting.

Direct compression tabletting, by virtue of its simplicity is obviously preferred when it is possible to use. However, until now, the ingredient mixtures obtained by mere dry mixing generally did not exhibit adequate flowability and were not adapted to be fed directly to the tabletting machine to prepare tablets of uniform and acceptable properties.

Various attempts have been made to develop inexpensive, free-flowing powder carrier/binder materials for use in direct compression tabletting. U.S. Pats. Nos. 3,584,114, 3,725,556 and 3,873,694, each having a filing date junior to applicants' effective filing date, propose means for facilitating direct compression tabletting.

Cavalli et al. (U.S. Pat. No. 3,584,114) describe combining "poor flowing" powders (e.g., cornstarch) with melted waxy like edible materials such as stearic acid, Carbowax, glyceryl monostearate and the like. These patentees confirmed what applicants have already pointed out, that is, that a typical cornstarch is a poor flowing powder and requires improvement in its flowability to be useful in direct compression tabletting. The method disclosed by these patentees is complex, and requires additional ingredients.

Hanssen et al., U.S. Pat. No. 3,725,556 describe a method of direct compression tabletting which includes spray drying the inert ingredients and the active ingredients after inert gas foaming to avoid the conventional granulation step. The inert ingredients required by these patentees include finely divided silica or alumina, an inert filler which may be water-insoluble rice starch or cornstarch or an alkaline earth metal phosphate, and some amount of a water soluble binder which may be water soluble starch, or other named substances. Applicants' issued U.S. Pat. No. 3,622,677 was cited as prior art against the subject patent. It should be appreciated that applicants' free-flowing precompacted-starch powder provides all the functions in direct compression tabletting which are described for the more complex combination of ingredients disclosed by Hanssen et al.

More recently, U.S. Pat. No. 3,873,694 has described a direct compression tabletting composition which comprises a crystalline sugar admixed with a maltodextrin and sprayed with an aqueous solution of a maltodextrin. The patent reinforces applicants' statement regarding direct compression tabletting, and sets forth the ideal properties needed in a "direct compression vehicle." It is interesting to note that Example 9 of this patent describes an experiment to determine the effect of the precompacted-starch (STA-Rx 1500) of the subject invention on direct compressed tablets made using a granulated tabletting vehicle.

STA-Rx 1500 was used in an amount of 10% by weight to the weight of the total mixture. In those tablets having an active medicinal ingredient, STA-Rx 1500 displaced a portion of the granulated tabletting vehicle.

Table 10 of the subject patent clearly shows the improved disintegration effect obtained when STA-Rx 1500 was used. In all cases where it was used, there was a decrease in disintegration time by about one third of the original time for the same tablet without the subject precompacted-starch powder (STA-Rx 1500). Friability and tablet hardness were also considered good. This example in U.S. Pat. No. 3,873,694 shows that the subject precompacted-starch powder is compatible within the described dextrose/maltodextrin based tabletting materials, and can be used in such tablets to improve disintegration time. However, it is even more noteworthy that the subject precompacted-starch powder can completely replace the more costly and complex "sole binder disintegrant" described and claimed in this patent. The pregranulation step required for the dextrose/maltodextrin material described in the patent is not required in the examples set forth below.

The limited acceptance of preparing compressed tablets by direct compression has stemmed principally from the unavailability of suitable and inexpensive direct compression binding agents. Of those materials which do qualify by reason of their binding properties, moreover, few are characterized by satisfactory overall properties. For example, one widely used binder material used in direct compression tabletting is spray-dried lactose. However, it is unacceptable in many uses because of its marked tendency to turn brown on aging. Because of such problems, most direct compression tabletting has required costly techniques such as the wet and dry granulation methods. As pointed out above, the search has continued to develop improved binder materials for use in direct compression tabletting. One major difficulty for which various solutions have been offered, is that many good binders and materials which tablet well do not dissolve properly when the tablet is used. They merely become glutinous globs in liquid, and do not release the active ingredients effectively.

DESCRIPTION OF THE PRIOR ART

One must appreciate that a good direct compression tabletting material should have the following properties:

(1) uniform sized particles which have free flowability, to facilitate preblending with active ingredients and loading of the tabletting machine;
(2) proper bulk density to provide uniform compressibility to produce tablets of high hardness, low friability and uniform dosage, and which remain constant in size after tabletting, and will withstand the required handling;
(3) inert material compatible with active ingredient and suitable for oral ingestion;
(4) effective disintegration rate; and
(5) ready availability at low cost.

The goal of the tabletter is to simplify the steps required, and decrease the number of substances which are required to provide all the properties needed in a tabletting material for successful direct compression tabletting. A single, direct compression tabletting material which has all of the above properties, and which can be used as the sole binder-disintegrant without other adjuvants is the ideal direct compression tabletting vehicle.

U.S. Pat. No. 2,098,293 describes a method of making dustless brewer's grits from starch by means of steam heated rolls operated at a temperature of 290° F. No "more than 2.7% soluble substances" are contained in this product, which is intended to be subsequently pasted and used for malting. Applicants have found that such materials cannot be successfully tabletted by direct compression tabletting.

The brewer's grits materials were pulverized and attempts were made to tablet them in a Colton 204 rotary press direct compression tabletting machine having ⅜ inch diameter cup punches and dies. Only a few underweight tablets could be made having hardness values of 0.3 kg or less, and the tablets which were obtained exhibited 100% friability (% weight loss) when tested on a Roche Friabilator.

Hansen et al. described physical modification of starch in U.S. Pat. No. 2,464,081 by means of differential roll milling, but in each example, care is taken to preserve the granular structure of the starch to avoid "objectionable fusing of the granules." Alum or formaldehyde may be added as a toughening agent to aid in avoiding undesirable fusing of starch granules during the treatment. The cold water dispersibility of the resulting starch ranged from 74% up to 100%. Applicants have found that such highly cold water soluble starch materials, when compressed into tablets, do not disintegrate satisfactorily in water. Upon being wetted, the surface of the tablet wets rapidly, and the tablet becomes a gummy mass which is not effective for dispensing an active ingredient, since the main portion of the active ingredient remains trapped in the gummy mass.

Racz et al. have described the testing of tablets with various starches in an article in Orvasi Szemle 6, 238-41 (1960); Chemical Abstracts 54:2314f. The method of tabletting is not disclosed, and the highest level of hardness achieved was 661 grams. Including the dead weight of hardness testing apparatus (75 grams), the hardest tablets may be Racz et al. (potato starch tablets) had a compressive strength of less than 0.74 kg. Tablets made from the precompacted-starch powder of this invention have a minimum hardness index of 4 kg., which is more than five times as hard, and the subject precompacted-starch powder can be employed in direct compression tabletting apparatus. Racz et al. give no description of flowability properties of their starch, or any preparation steps which may have been required.

Protzman et al., in U.S. Pat. No. 3,137,592, describe extruding starch to obtain an homogeneous gelatinized starch product having no birefringence or starch granule structure. The extrusion is performed at elevated temperatures in the presence of a starch swelling agent to insure that the starch becomes completely gelatinized.

Kessinger (U.S. Pat. No. 3,171,747) describes a baker's dusting composition which is a mixture of 70–50% by weight of granular starch and 30–50% by weight of gelatinized starch. The granular starch also contains from about 0.5 to 0.05 percent by weight of an edible oil. Kessinger states that his gelatinized starch may be made according to the method of Protzman et al., described above. When applicants attempted to make tablets with the Kessinger baker's dusting composition, it did not have sufficient flowability to be useful in direct compression tabletting. Only underweight tablets could be produced because of the low bulk density of this blended material, and the resulting tablets which could be made by operating the tabletting machine by hand were 100% friable. The hardness index for these tablets was only 0.7 kg., compared to a hardness index of more than twenty one times harder (14.9 kg.) for tablets made at the same time using the same direct compression tabletting apparatus, and using the precompacted-starch powder of the subject invention. In addition, the tablets made with the Kessinger composition did not disintegrate, even after one hour, whereas the tablets made with the precompacted-starch powder of the subject invention having 14.9 kg. hardness disintegrated effectively within less than eight minutes under the same test conditions.

Tablet disintegrants to accelerate disintegration are disclosed in U.S. Pat. No. 3,034,911 issued May 15, 1962. The disintegrants disclosed are chemically modified starches including cold water dispersible starch phosphates, starch sulfates and carboxymethyl starch ether. These modified starches are intentionally kept in completely ungelatinized condition to better perform their function of accelerating disintegration. The preferred level of the "accelerator" in tablets is about 3% to 20% by weight, and in each formulation tabletted, another tabletting agent was also present. Several examples included spray dried lactose, another included methylcellulose, one included talc and another employed gum arabic as a binder. It further appears that either a dry or wet granulation was required in each case prior to tabletting. There is no suggestion by McKee et al. that a single, chemically unmodified precompacted-starch powder can serve the two functions of binder and disintegrant, and that the granulation steps in tabletting can be eliminated.

Kott et al. describe a method of making "dustless" starch by compacting in U.S. Pat. No. 3,119,719. Care is taken to avoid any gelatinization, since it changes the character and performance of the starch. The screen size for the product is between about 3 mesh to about 20 mesh.

U.S. Pat. No. 3,399,081 issued Aug. 27, 1968 describes a solvent process for preparing pregelatinized starch using the gelatinizing effects of liquid ammonia in nonaqueous media, including methanol, ethanol, 1-propanol and other nonaqueous solvents. The stated goal of the method is to produce a 100% gelatinized starch product useful in textile and paper sizing, ink thickener, adhesives and various food uses. Such completely gelatinized starches are not useful as binder-disintegrants in direct compression tabletting because the resulting tablets do not dissolve effectively, but instead form a gummy mass with a dry center. Swelling power by itself does not determine what starch materials will be useful in tabletting.

A binder-disintegrant comprising non-granular amylose is disclosed in U.S. Pat. No. 3,490,742 issued Jan. 20, 1970. This material is prepared either by fractionating starch or by dissolving granular high amylose starch in water at an elevated temperature. The cost of non-granular amylose or fractionated amylose which is then gelatinized is excessive when compared to the cost of the precompacted-starch powder of the subject invention.

In view of the above, it can be seen that precompacted-starches constitute a known class of materials. They are prepared by subjecting a granular starch raw material to pressure in the presence of water to effect distortion and fracture of at least some of the granules and produce adhesion between particles of the resultant mass. The resultant compacted material may have differing cold-water swelling properties and contain varying amounts of cold-water soluble material depending primarily upon the particular pressure, temperature, and moisture conditions utilized. Specific techniques commonly employed include passing the starting starch through the nip of rotating rolls operating at the same or different speeds, as described in U.S. Pat. Nos. 2,098,293; 2,168,524; 2,464,081; and 3,196,044, and working the starch in the course of an extrusion operation as shown in U.S. Pat. Nos. 3,137,592 and 3,159,505. Compacted starches heretofore have found utility primarily as "dustless" carbohydrate nutrients in the brewing industry and as binders in the preparation of rough-molded products containing relatively coarse aggregate materials such as foundry cores and charcoal briquettes.

SUMMARY OF THE INVENTION

The present invention provides a freely flowable binder-disintegrant precompacted-starch powder most useful in direct compression tabletting. In addition, it is less expensive to manufacture than other direct compression tabletting vehicles, and allows elimination of the pregranulation steps required with other tabletting materials which do not have the flowability needed in direct compression tabletting apparatus. The tablets made using the improved tabletting vehicle of this invention are hard, non-friable, and readily disintegrate in an aqueous medium.

The free flowability and size characteristics of this precompacted-starch powder also have proven to be most useful in blending with an active ingredient as an inert filler material in dry powder-containing gelatin capsules. The ingredients blend uniformly to provide uniform dosage loading of the capsules, and the inert, precompacted-starch powder disintegrates rapidly without interfering with the active ingredient when the capsules are ingested.

The precompacted-starch powder of the present invention has been subjected to physical compaction under high moisture conditions without supplementary thermal energy to obtain a precompacted-starch comprising birefringent and non-birefringent fragments of granules in which some aggregates of granules and fragments are present, and having a cold water solubility of from 4% to about 40% by weight, preferably 6%-20% by weight, and a moisture content of from about 9-16%, total weight basis. The precompacted-starch is then ground, or pulverized, and screened to obtain a free-flowing powder material having a bulk density of about 0.5 to about 0.70 grams per milliliter, and essentially free of +40 mesh particles. At least 90% of the particles are −80 mesh size, at least about 10% are +270 mesh size, and about 30% to 90% are −270 mesh size on a total weight basis.

Tablets made using the subject precompacted-starch powder as the sole binder-disintegrant in combination with an active ingredient have a hardness index of at least about 4 kilograms, a friability weight loss less than 1.0% a swelling power of 2.5 to about 12 and the tablets disintegrate effectively in an aqueous medium to release the active ingredient.

It now surprisingly has been discovered that certain precompacted-starch powders, described more fully hereinafter, advantageously are characterized by properties which enable them to be dry mixed with active ingredients and conventional tabletting aids, such as fillers, lubricants, and the like, to prepare active ingredient-containing formulations which are directly compressible into tablets in conventional tabletting equipment. The present invention therefore provides a highly valuable means whereby tabletting operations may be greatly simplified, and the troublesome and time-consuming preliminary granulation and slugging steps which characterized most tabletting operations heretofore available may be eliminated. The precompacted-starch powders employed in the present invention, moreover, advantageously are characterized by properties which satisfy both the requirements of a binder for the active ingredient and a disintegrant for the tablet in aqueous media. Consequently, suitable direct-compression tablets of satisfactory hardness, friability, and disintegration properties advantageously may be prepared by means of the present invention using the precompacted-starch powders as a sole, dual-functioning binder-disintegrant, and the heretofore commonly required practice of adding separate ingredients as the binder and disintegrant with the attendant problems of properly mixing multiple ingredients and balancing dosage levels no longer need be followed. The starch binder-disintegrant ingredient employed in preparing direct compression tablets in accordance with the present invention, furthermore, easily and cheaply may be obtained from readily available and inexpensive starting raw materials, namely granular starches. Of such binder-disintegrant-compacted-starches, many embodiments are characterized by low color, color stability, and acceptability for human consumption. The present invention, therefore, includes what may be said to be a "universal" ingredient for direct-compression tabletting, whereby a wide range of active ingredients, including many pharmaceuticals tabletted heretofore only with great difficulty, if at all, now easily and inexpensively may be satisfactorily tabletted by direct compression.

Figure 1:
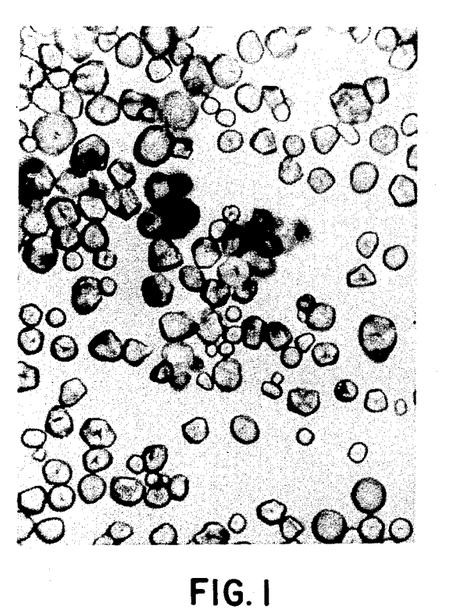
FIG. 1 is a photomicrograph, taken under bright-field illumination of ordinary corn starch at a magnification of 425.
Figure 2:
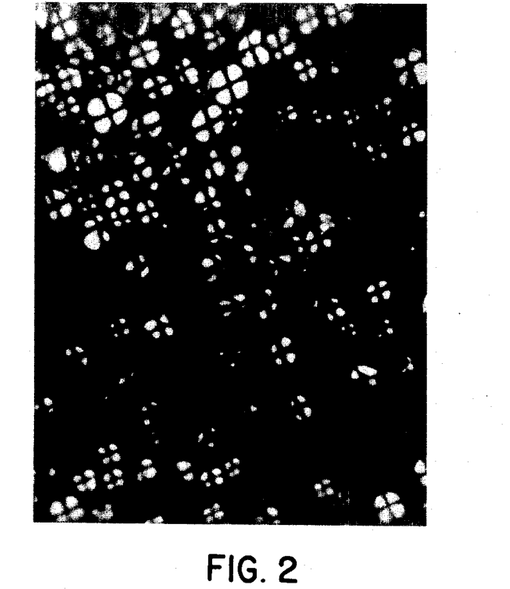
FIG. 2 is a photomicrograph corresponding to FIG. 1 but with the light polarized.

The precompacted-starch powders employed in the practice of the present invention are derived from appropriately compacted granular starch raw materials and are superficially dry, free-flowing, partially cold-water soluble materials which swell in cold water and have a relatively high loose bulk density. The powders themselves are directly compressible in conventional tabletting equipment into relatively rapidly disintegrative placebo tablets of high hardness and low friability. Microscopic examination of the precompacted-starch powders reveals the starch content of the materials to comprise a combination of both birefringent granules and non-birefringent fragments of granules, in which some aggregates of granules and fragments are present. These characteristics of the precompacted-starch powders on microscopic examination are apparent from the photomicrographs reproduced in FIGS. 1–4. In FIG. 1 granules of ordinary corn starch are shown as viewed with unpolarized light at 425 magnification. FIG. 2 shows the same granules viewed with the light polarized at the same magnification. It will be noted that in FIG. 2 the granules all exhibit birefringence (i.e., the crosses) which is characteristic of starch granules.

BRIEF DESCRIPTION OF THE DRAWINGS

For a more complete understanding of the nature and scope of the invention reference may now be had to the following detailed description thereof with illustrative working examples, and to the accompanying drawings wherein.

DETAILED DESCRIPTION OF THE INVENTION

Figure 3:
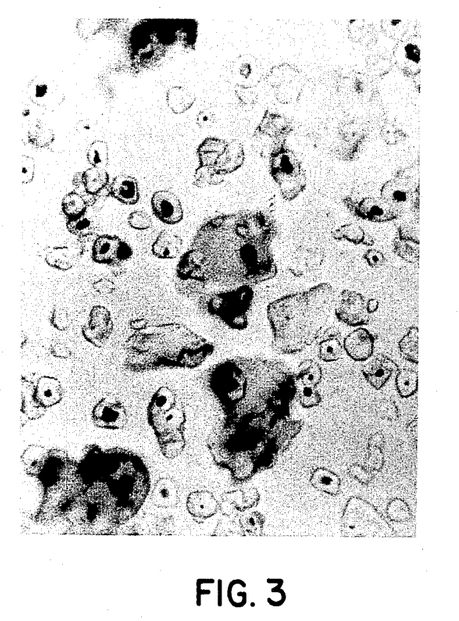
FIG. 3 is a photomicrograph, taken under bright-field illumination of precompacted-cornstarch, useful in accordance with the present invention, at a magnification of 425.
Figure 4:
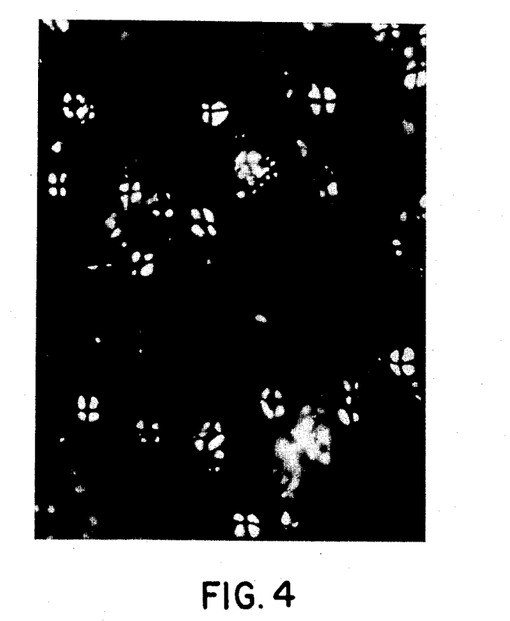
FIG. 4 is a photomicrograph corresponding to FIG. 3 but with the light polarized.

In FIG. 3 a sample of precompacted-starch powder, which is directly compressible into tablets in accordance with this invention, is shown as viewed with unpolarized light at 425 magnification. A number of starch granules appear in FIG. 3 along with aggregates and granular fragments. When the same sample of precompacted-starch powder is viewed under polarized light at the same magnification, it is clearly seen that the sample is a combination of birefringent granules and non-birefringent fragments of granules, in which there are aggregates of granules and fragments.

Precompacted-starch powders of the invention have the following characteristics:

| Property | Broad | Preferred |
|---|---|---|
| Cold-water Solubility, % | 4–40 | 6–20 |
| Swelling Power | 2.5–12 | 3.5–10 |
| Loose Bulk Density, g/ml | 0.50 minimum | 0155–0170 |
| Placebo Tablet (Direct Compression Properties) | | |
| Hardness, kg. | 5 minimum | 8 minimum |
| Friability, % wt. loss | 1.0 maximum | 0.5 maximum |
| Disintegration Time, min. (in water) | 30 maximum | 15 maximum |

As used herein, the term "superficially dry" is intended to indicate a powder is dry in the visual and tactile sense. A "placebo" tablet is a tablet prepared by directly compressing one material alone such as a compacted-starch powder. The terms "cold-water solubility," "Swelling power," "hardness," "friability," "disintegration time," and "granular starch raw material" are defined as follows:

Cold-water solubility — The percent by weight of the starch dry substance which dissolves in water at 25° C. when determined by the following procedure: One gram of the starch product being tested is added to 100 ml. of water at 25° C. in a high-shear blender and mixing is carried out at 1,500 r.p.m. for two minutes. The resultant sample is then transferred to a 250 ml. round-bottom centrifuge tube and centrifuged for 15 minutes at 2,000 r.p.m. A 25 ml. aliquot of the clear centrifugate is transferred to a tared aluminum pan and evaporated to dryness on a steam bath. The dish is then dried to a constant weight at 110° C. The weight of the dried material in the pan multiplied by 400 and divided by the dry substance weight of the original sample is the cold-water solubility of the starch material. By this test commonly available granular starches are essentially cold-water insoluble, generally containing less than about 2% by weight cold-water solubles and in the case of unmodified starches less than about 1%.

Swelling power — a measure of the ability of a starch to swell in cold water as determined by Method 56-20 of "Cereal Laboratory Methods" published by the American Association of Cereal Chemists. For reference purposes, uncompacted granular starches generally have a swelling power on the order of about 2.

Hardness — a measure of the strength of tablets (average of ten or more tablets) and their ability to retain their physical integrity, expressed in terms of kilograms, as determined by the conventional procedure using a Model B tablet hardness tester of the Strong-Cobb-Arner Company, Cleveland, Ohio, to obtain an indicated pressure gauge reading at fracture of the tablet (tablet mounted on edge in tester) and multiplying the indicated hardness value by a factor of 0.78 to convert the gauge reading to actual pressure. For example, a satisfactory active ingredient-containing tablet generally should have a hardness in this test of at least about 4 kg.

Friability — a measure of the tendency of tablets (average of ten or more tablets) to crumble and dust, expressed in terms of percent weight loss, as determined by the "Roche" test described in the *Journal of the American Pharmaceutical Association*, Scientific Edition, Vol. 45 pages 114–116 (1956). For reference purposes, an active ingredient-containing tablet displaying a weight loss of less than about 1.0% generally is considered to have acceptable friability.

Disintegration time — the time observed for tablets (range of six tablets) to disintegrate in water as determined by a modification, in which the use of discs is eliminated, of the procedure for uncoated tablets described in Pharmacopeia of the United States of America, 16th Edition, 934–936 (1960).

Granular starch raw material — the starting starch which has been compacted in the preparation of the precompacted-starch powders of the invention. The starting starch suitably may be any granular starch derived from the root, stem, or fruit of a plant. Specific examples of starch-yielding sources include corn, rice, wheat, potato, tapioca, and arrowroot. The starting starch raw material suitably may be unmodified, modified, derivatized, or cross-linked. Examples of unmodified starches are the granular starches conventionally prepared from natural starch sources by removal of fiber, gluten, and other proteinaceous impurities, with or without subsequent washing, drying, screening, bleaching and/or sterilization. Modified granular starches include thin-boiling starches made by heating a water slurry of an unmodified starch below the gelatinization temperature with a mineral acid (e.g., hydrochloric acid) or an oxidizing agent (e.g., alkaline hypochlorite). Derivatized granular starches include starch esters, e.g., starch acetate and starch propionate, and starch ethers, e.g., hydroxyethyl, carboxymethyl, and cyanoethyl starch, prepared from unmodified or modified granular starches with retention of the granular structure. Granular cross-linked starches include ungelatinized starch products made by reacting an unmodified, modified, or derivatized granular starch with a polyfunctional reactant, e.g., phosphorous oxychloride or epichlorohydrin.

FLOWABILITY TEST

The free-flowing property of the precompacted-starch powders employed in the invention is exemplified by the ability of the powders to meet the following arbitrary test: a sample of powder being tested is poured into a 24/40 standard taper glass powder funnel, the tip of which is suspended normal to, and one inch above, a horizontal, dry smooth paper surface. Powder is poured through the funnel until the cone of powder formed on the paper surface below reaches the tip of the funnel, and the funnel plugs. The average radius of the cone base is determined by taking four radius measurements from the funnel tip along diameters intersecting at right angles and averaging the values. From the cone height (1 inch) and the average radius of its base, the angle formed by the inclined surface of the powder cone and the horizontal, herein referred to as the "angle of repose," can be determined using well known trigonometric principles, i.e. by calculating the tangent of the angle of repose. A powder which is not free-flowing in the sense of the term as employed herein displays an angle of repose in this test of more than about 40°. The more preferred free-flowing characteristics are displayed by precompacted-starch powders forming an angle of repose in the range of from about 20° to about 35°.

Due to the availability and low cost of the starting raw material required, precompacted-starch powders derived from corn starch, and more preferably, an unmodified corn starch, constitute the binder-disintegrant ingredients preferred for utilization in the present invention. Such starch raw materials, moreover, provide resultant binder-disintegrant ingredients which display excellent color stability during storage and in the ultimate tablet. By reason of the excellent over-all properties of tablets which can be obtained by the use thereof, the particularly preferred binder-disintegrant ingredients are superficially dry, free-flowing powders of the above-described type characterized by a cold-water solubility of from about 6 to about 15% and a swelling power of from about 5 to about 8 and being derivatives of a bleached native corn starch, e.g., hypochlorite-bleached native corn starch.

The starch binder-disintegrant ingredients employed in the present invention are prepared from the starting granular starch raw materials by the same basic steps heretofore utilized in preparing powders of compacted starches and in general involving compacting the starting starch raw material in the presence of water, comminuting the resultant compacted material, and classifying the comminuted intermediate into the desired particle size fraction.

The compaction step suitably may be carried out in any convenient device conventionally employed for this purpose. As described above, the more commonly used devices include differential roll mills, concurrent roll mills, extruders, and the like. The moisture content of the granular feed starch and the temperature which the starch attains during the compaction are important variables in achieving a suitably modified compact. In preparing compacted starches suitable for use in the present method, temperatures should be limited to those below the gelatinization temperature of the particular starch used. Higher temperatures provide compacts which, when comminuted, yield powders which are over-gelatinized and have poor disintegrant properties. Optimum compaction conditions generally include temperatures in the range of from about 20° to about 50° C., and a moisture content in the range of about 15%–50% by weight, based on the weight of the starch.

The water content of the granular starch feed must be in the range whereby the properties of the granular starch feed are altered to the desired degree in the compaction treatment. For a given starch and a given compaction device, limits for the moisture content will exist at which the starch feed is either too dry or too wet for the compaction to sufficiently change the properties of the starting starch. For a given starch and compacting device, however, the operable and optimum water content ranges easily may be determined in the manner known and described hereafter, i.e., varying the feed starch moisture content and noting the degree of starch modification achieved in terms of the effect on the cold-water solubility and swelling power of the starch. As a general rule, in most conventional starch compaction equipment, water content in the feed granular starch in the range of from about 15 to about 50% of the starch total weight is used to achieve the desired amount of compaction. The lower moisture levels in this range, e.g., from about 15 to about 30%, are generally more adapted for use in roll-type compaction equipment such as differential roll mills, and the higher water contents in this range, e.g., from about 30 to about 50%, are better adapted for use in devices effecting the desired working in a confined space such as in a screw-containing barrel-type extruder. Since commonly available granular starches generally have a moisture content on the order of 10–12%, water usually must be added to the granular feed starch prior to compaction.

While, as stated above, the particular compaction technique employed in preparing the starches employed as binder-disintegrants in the present invention is not critical, a compaction method which is particularly useful is exemplified by that disclosed in U.S. Pat. No. 2,464,081 entailing the use of a differential mill. In a typical application of this technique, a granular starch feed having an adjusted moisture content in the range of from about 24 to about 32% by weight is fed through the mill operated with a gap between the rolls in the range of 3 to 12 mils. Typical roll speeds vary between 35 to 70 feet (linear) per minute using a speed differential of from about 10 to about 20 feet per minute. Roll temperatures maintained by circulating water through the rolls generally vary between about 10° to about 40° C. More than one pass through the rolls generally is required to sufficiently modify the starting starch properties with up to four passes being common.

Another particularly useful compaction technique utilizes a rotating pellet mill which is adapted to subject the starch feed to a sufficient amount of working during the formation of pellets therefrom. An example of a typical pelleting operation which achieves suitable compaction generally employs a pellet mill having dies 3/16 inch in diameter and 1½ inches in length in which the starting granular starch at a moisture content of from about 15 to about 30% by weight is pelletized at a feed rate of 900 to 1,000 lbs. per hour with the mill rotating at 125-150 r.p.m. Advantages of utilizing a pellet mill are that one pass through the mill usually is sufficient to provide the desired starch modification and that a significantly reduced amount of fines is produced as compared to most other compaction techniques.

The material produced by the required amount of compaction then is ground and screened to a suitable particle size, the moisture content being adjusted during the recovery of the desired powder from the compact. For optimum results, the compact is dried prior to being ground. Drying lessens the proportion of fines produced in the grinding step and guards against possible further undesirable starch alteration during grinding. In the drying, the moisture content of the compacted material is commonly reduced to from about 4 to about 14% by weight.

The grinding suitably may be carried out in any grinder, mill or combination of comminuting devices adapted to reduce the compact to a free-flowing, directly compressible powder. It has been found that the more suitable tablet binder-disintegrant powders are those which are relatively fine. In the grinding step, therefore, the compacted starch generally is reduced to a powder of which at least about 30% of the total weight thereof is material of −270 mesh. The term "mesh," as used herein, refers to the U. S. Standard Sieve Series, A.S.T.M. Specifications. The pressure of too great a proportion of fines is not conducive to optimum tabletting so it generally is preferred to control grinding to provide a powder containing less than about 90% by weight material of 31 270 mesh. The more preferred powders obtained in the grinding step, by virtue of the properties of the tablets obtained therefrom and their adaptability to tabletting machine operation, are those ground to form about 45 to about 75% by weight material of −270 mesh. A specific grinding technique suitable for use involves initially grinding the compact to −10 mesh and then completing grinding in a mill adapted to recycle all +100 mesh material.

The water content of the precompacted-starch powder has an effect on the binder-disintegrant properties of the material. Too low or too high a water content detracts from the properties of the ultimate tablets formed. Generally moisture contents in the range of from 9 to about 16% of the powder total weight are suitable with the more preferred results usually being obtained at moisture contents in the range of from about 11 to about 13% by weight. Accordingly, following grinding, the moisture content of resultant powder preferably is adjusted, if necessary, by drying or the addition of water.

As stated the binder-disintegrant starch powders preferred for use contain a low proportion of coarse particles. Generally, it is desired that the powder contains less than about 10% by weight material of +80 mesh. The more preferred powders are essentially free of +40 mesh material and contain less than about 5% of material of 40-80 mesh. The preferred materials, therefore, are screened to −40 mesh and preferably −80 mesh before actual use. Screening is particularly desirable if the powder from the grinding step subsequently is moistened to adjust its moisture content since the moistening step increases the amount of +80 mesh material in the powder. Oversize material can be ground to the desired smaller particle size material.

Typical precompacted-starch powders suitable for use in the present invention here are characterized by the following particle size distribution:

| Particle Size | Proportion of Powder, % total weight |
|---|---|
| 40-80 mesh | 0-5 |
| 80-200 mesh | 5-30 |
| 200-270 mesh | 10-40 |
| through 270 mesh | 45-75 |

At least 10% should be between 80 and 270 mesh to help in imparting free-flowing characteristics.

In the preferred preparation of tablets by the present invention, an active material ingredient is thoroughly mixed by any suitable dry blending technique with any of the above-described precompacted-starch powders in relative amounts required to provide a resultant superficially dry, free-flowing formulation directly compressible into tablets, and the formulation then is tabletted by direct compression.

Active ingredients contemplated to be employed in the preparation of tablets by the present invention constitute all active ingredients compatible with the above-described compacted-starch powders in formulations directly compressible into tablets. The present invention is particularly adapted for use in preparing tablets containing pulverulent pharmaceutically-active materials. Specific examples of pharmaceutically-active ingredients which advantageously may be tabletted by the present invention include ascorbic acid, sodium p-aminosalicylate, phenacetin, and N-acetyl-p-aminophenol, all materials which heretofore generally have been tabletted only with great difficulty. The particular nature of the active material is not critical, however, and non-pharmaceutical active materials, e.g., pulverulent detergents, dyes, pesticides, and foods, forming directly compressible mixtures with the compacted-starch powders can also be employed.

The amount of active material ingredient employed in preparing tablets according to the present technique depends, inter alia, upon the nature and relative compatibility of the active material, and the end use for which the tablet is desired, the latter dictating thereby the tolerable properties in terms of hardness, friability, and/or disintegratability of the final tablet. Given the minimum and preferred characteristics desired in the final tablet, the tolerable limits on the weight ratio of active ingredient to binder-disintegrant for a particular active ingredient easily may be determined by the known technique of sequentially increasing the active ingredient content of the tablet. In general, acceptable active material-containing tablets are those which display a hardness of at least about 4 kg., preferably above about 5 kg., and a friability corresponding to a weight loss of less than about 1.0%, preferably less than about 0.5%. For a tablet having suitable friability, a lower hardness generally can be tolerated.

Depending upon the type and contemplated use of the final tablet, the disintegration requirements may vary over a wide range. A particular feature of the present invention is that a wide range of active ingredients may be tabletted to provide tablets displaying disintegration times in aqueous media of generally less than 30 minutes and more usually less than 15 minutes and in the range of from about 0.5 to about 10 minutes. The rapid disintegration rates of tablets prepared by the present method, as stated, stem from the advantageous characteristics of the precompacted-starch powders to function not only as excellent binding agents but as agents which accelerate tablet disintegration as well. In general, specific embodiments of tablets prepared in the invention contain from about 5 to about 90% by weight active ingredient, dry substance basis. An additional feature of the present invention is that, by the use of the binder-disintegrant precompacted-starch powders, even many pulverulent active ingredients which themselves are non-compressible or only poorly compressible, exemplified by the pharmaceuticals named, may be formed into suitable tablets containing from about 20 to about 50% and above of the active ingredient based on the tablet dry substance weight.

Adjuvants, such as tabletting lubricants, fillers, anti-sticking agents, coloring agents, and the like conventionally employed in preparing particular tablets by direct compression, suitably may be incorporated in appropriately effective amounts into the compressible formulations formed in the present invention. A lubricant such as talc, magnesium stearate, or stearic acid, when employed, generally is added in an amount ranging up to about 10% by weight of the total tabletting formulation. Colloidal silica constitutes a typical antisticking agent or so-called "glidant." A glidant such as colloidal silica, when incorporated in a formulation, usually is added in an amount ranging up to about 2% of the formulation total weight. Fillers, which may also function as supplemental binders or disintegrants, where employed, must not be added in amounts which impair undesirably the direct compressibility of the tabletting formulations.

While the precompacted-starch powders employed in the present invention are capable of satisfying the dual requirements of a binder-disintegrant, the present invention, as stated, also contemplated embodiments wherein effective amounts of another direct-compression binder such as lactose and the like and/or a separate disintegrating agent such as native corn starch also is incorporated into the formulation. In most cases, however, the addition of such additional binder is unimportant in view of the excellent characteristics of the binder-disintegrant precompacted-starch powders of this invention. In view of this, it will be understood the present invention is directed primarily to embodiments wherein the superficially dry, free-flowing binder-disintegrant starch of this invention is the major binder ingredient employed, i.e., present in an amount corresponding to at least 50% of the total weight amount of tablet binding agent employed, and more preferably is the sole binding agent added to the formulation for this purpose. In some instances, a supplemental disintegrant may provide some improvement. An example of this is in the preparation of tablets of sodium p-amino-salicylate dihydrate wherein the disintegration rate of the tablet advantageously may be further accelerated by the addition of a conventional granular starch disintegration aid.

The more desirable tablets are prepared from superficially dry formulations containing from about 5 to about 15% moisture based on the formulation total weight. Accordingly, appropriate adjustment of the moisture content may be made, where necessary or desirable, during the formulation operation to improve the tabletting characteristics of the mixture. It may also be desirable, after mixing the ingredients, to screen the formulation to remove all oversize particles introduced in the active ingredient or tabletting aids and thereby to improve tabletting efficiency. In this respect, removal of +40 mesh particles by screening generally is desirable.

In accordance with the present invention, any conventional single or rotary tablet making apparatus suitably may be employed in the tabletting operation. As is standard in conventional tabletting practice, optimum results are obtained for particular formulations by the use of the highest pressure settings consistent with good tablet press operation.

Tablets prepared from a given batch of tabletting formulation by means of the present invention are essentially uniform in thickness, weight, and active ingredient dosage level and have excellent surface smoothness as indicated by the lack of pits and cracks. A further characteristic of the tablets made according to the invention is that a substantial duplication of tablet properties is obtained by grinding the tablets to a free-flowing powder and retabletting.

While the above discussion has been limited to the preparation of tablets by direct compression, it further will be understood that the described free-flowing, directly compressible, active ingredient and precompacted-starch powder-containing formulations, of course, also can be employed in the preparation of compressed tablets either by the double compression technique wherein slugs initially are prepared from a formulation and the slugs subsequently dry granulated to prepare tablet machine feed material, or by the wet granulation method wherein a wetting agent, such as water, is added to a formulation, the moistened mass is dried without gelatinizing the compacted-starch powder ingredient, and the resultant dried material is ground into granular feed for the tabletting machine. Compressed tablets which can be prepared by either method have essentially the same characteristics as those produced by direct compression. In view of the adaptability of the formulations prepared hereby to direct-compression tabletting, however, the dry and wet granulation methods are impractical and can be anticipated to be rarely, if ever, employed.

The invention having been described in detail, the following examples are presented to show specific embodiments thereof. It will be understood the examples are given for illustration purposes only and not by way of limitation.

EXAMPLE I

This example illustrates the preparation of suitable tablet binder-disintegrant starches from an unmodified corn starch and the use of the binder-disintegrant starches in the preparation of tablets by direct compression.

Three samples of ground hypochlorite-bleached native corn starch (Starch A) having the properties set forth in Table 1 were converted to precompacted-starch powders by three different techniques. The techniques employed were as follows:

TECHNIQUE 1 (PELLETIZING)

One sample of the hypochlorite-bleached native corn starch was moistened to a water content of 24–25% by weight and the moistened starch was pelletized at a rate of about 960 pounds/hour on a California Process Series (CM-FB Master pellet mill having dies 3/16 inch in diameter 1½ inches in length and operated at about 130 r.p.m. The resultant pellets (¼ inch length) were then dried in a rotary drier to 7.4% by weight moisture. The dried pellets were then ground to −10 mesh in a Model DS−6 Series 1606 stainless steel Fitzmill grinder, and the −10 mesh material was further ground to −100 mesh in a Model PC 20 Strong-Scott Pulvocron grinder operated at 3,500 r.p.m. with the classifier at 1,000 r.p.m. and the tailings return at 100%. The resultant powder was remoistened to 11.5-12.5% by weight water in a horizontal ribbon blender, and the moistened material was screened to −40 mesh. The properties of the resultant precompacted-starch powder (Starch $A_p$) are set forth in Table 1.

TECHNIQUE 2 (DIFFERENTIAL ROLL-MILLING)

The second sample of the ground hypochlorite-bleached native corn starch was compacted, after being moistened to a water content of about 25-2% by weight, in an EEMCO Laboratory differential roll mill having 12 in. length rolls of 6 in. diameter. The mill was operated with a mill gap of 12 mils, and roll speeds of 50 and 70 linear feet/min. on the respective rolls. Roll temperature was maintained at about 23° C. by cooling water circulating through the rolls. The compacted starch sheet stripped from the rolls was then subjected to three additional passes through the mill. The resultant compact was then dried to a moisture content of 6-9% by weight. The dried compact was ground first to less than about 1.0 mm in a Wiley mill and then to less than about 0.5 mm in a Raymond hammer mill. The ground material was then remoistened with water to a moisture content of 11.8% by weight, and screened to −80 mesh. The resultant precompacted-starch powder (Starch $A_{A.C.}$) had the properties set forth in Table 1.

TECHNIQUE 3 (COMPACTION IN ALLIS-CHALMERS COMPACTER)

The third sample of the ground hypochlorite-bleached native corn starch was adjusted to a moisture content of 21.6% by weight and then treated using force feeding in a compacter manufactured by Allis-Chalmers Corp. having rolls 24 inches in diameter and 8 inches in length. The compacter was operated with the rolls at ambient temperatures, a roll gap of 0.05 inch, a roll speed of 2.5 r.p.m., a force feeder speed of 15 r.p.m., and a starting bearing pressure of 1,000 p.s.i.g. The ribbon-like compact obtained was dried to 7% by weight water and then ground as in Technique 2 above. The ground material was then adjusted to a moisture content of about 12.0% by weight, and then finally screened to −80 mesh. The properties of the resultant precompacted-starch powder (Starch $A_{A.C.}$) are set forth in Table 1.

Table 1

| Starch | Description | H₂O Content, % | Cold Water Solubility, % | Swelling Power | Loose Bulk Density, gm/ml | Flowability, Angle of Repose |
|---|---|---|---|---|---|---|
| A | Hypochlorite bleached native corn starch | 10.0 | 0.2-0.5 | 1.9-2.1 | 0.52-0.56 | 44-45 |
| $A_P$ | Pelletized Starch A | 12.4 | 9.2 | 6.6 | 0.57 | 33 |
| $A_{DRM}$ | Differential roll-milled Starch A | 11.8 | 13.1 | 6.8 | 0.60 | 31 |
| $A_{A.C.}$ | Roll mill compacted Starch A | 12.0 | 11.6 | 7.2 | 0.59 | 31 |

The data in Table 1 indicate that the three different compaction methods can each produce precompacted starch powders essentially equivalent in these properties.

Superficially dry tabletting formulations were prepared by thoroughly blending the resultant precompacted-starch powders, each in turn, with separate powdered preparations of ascorbic acid, phenacetin, sodium p-amino-salicylate dihydrate (NaPAS) and N-acetyl-p-aminophenol (APAP) in the proportions set forth below in Table 2, incorporating talc and/or colloidal silica (Cab-o-Sil) as tabletting aids into the formulations, and screening the resultant mixtures to −40 mesh. The free-flowing powders obtained were then directly tabletted on a Colton No. 204 fourpunch press manufactured by the Colton Division of Cherry-Burrell Corporation, Detroit, Michigan. A set of ⅜ inch diameter standard cap punches and dies was employed, and the press was operated at 35 r.p.m. to produce 140 tablets/min. The pressure setting of the press was increased in each run to a value consistent with good press operation as indicated by a "thump" in the tabletting. A sample of each of the precompacted-starch powders also was tabletted using the same tabletting procedure. The properties of the tablets obtained also are set forth in Table 2.

Table 2

| | | | Formulation Composition | | | | Tablet Properties | | |
|---|---|---|---|---|---|---|---|---|---|
| | | | Drug/Binder | Adjuvants, % by weight total formulation | | | | | |
| Tablet No. | Starch Binder | Drug | Weight Ratio* | Talc | Colloidal Silica | H₂O Content, % | Average Hardness, KG. | Average Friability % Wt. Loss | Disintegration Time, Min. |
| 1 | $A_P$ | — | 0:100 | — | — | 12.4 | 13.7 | 0.08 | 4.5-5.0 |
| 2 | " | Ascorbic Acid | 40:60 | 7.5 | 0.0128 | 7.3 | 5.9 | 0.19 | 1.5 |
| 3 | " | Phenacetin | 35:65 | — | 0.0092 | 8.4 | 5.9 | 0.44 | 2.5 |
| 4 | " | APAP | 40:60 | 6.0 | 0.0087 | 7.4 | 5.7 | 0.23 | 1.5 |
| 5 | " | NaPAS | 50:50 | 7.0 | 0.0096 | 13.3 | 6.4 | 0.39 | 70-80 |
| 6 | $A_{DRM}$ | — | 0:100 | — | — | 11.8 | 14.0 | 0.12 | 6.5-7.0 |

Table 2-continued

| Tablet No. | Starch Binder | Drug | Drug/Binder Weight Ratio* | Adjuvants, % by weight total formulation Talc | Adjuvants, % by weight total formulation Colloidal Silica | H$_2$O Content, % | Tablet Properties Average Hardness, KG. | Tablet Properties Average Friability % Wt. Loss | Tablet Properties Disintegration Time, Min. |
|---|---|---|---|---|---|---|---|---|---|
| 7 | " | Ascorbic Acid | 35:65 | 5.0 | 0.0082 | 7.7 | 4.5 | 0.37 | 2.0–2.5 |
| 8 | " | Phenacetin | 25:75 | — | 0.0091 | 9.1 | 5.4 | 0.35 | 4.0 |
| 9 | " | APAP | 25:75 | 3.0 | 0.0082 | 8.4 | 6.6 | 0.20 | 2.5–3.0 |
| 10 | " | NaPAS | 40:60 | 5.0 | 0.0082 | 13.3 | 5.8 | 0.51 | 60–90 |
| 11 | $A_{AC}$ | — | 0:100 | — | — | 12.0 | 14.7 | 0.1 | 9.0–9.5 |
| 12 | " | Ascorbic Acid | 30:70 | 5.0 | 0.0092 | 8.2 | 6.3 | 0.16 | 3.0 |
| 13 | $A_{AC}$ | Phenacetin | 30:70 | — | 0.0091 | 8.6 | 6.7 | 0.42 | 3.0–3.5 |
| 14 | $A_{AC}$ | APAP | 30:70 | 3.00 | 0.0093 | 8.4 | 7.2 | 0.43 | 2.5 |
| 15 | " | NaPAS | 35:65 | 3.5 | 0.0076 | 12.7 | 6.4 | 0.31 | 90–100 |

*Based on binder dry substance weight

The above data indicate that the precompacted-starch powders are directly compressible into tablets themselves and that suitably hard, non-friable, rapidly disintegrative tablets containing relatively high levels of heretofore difficult-to-tablet drugs, i.e., ascorbic acid, phenacetin, and APAP, advantageously can be prepared using the precompacted-starch powders as sole dual-functioning binder-disintegrant ingredients. Although the NaPAS-containing tablets disintegrated relatively slowly, these tablets had suitable hardness and friability properties; the precompacted starches are satisfactory binders even of this previously difficult-to-tablet drug.

EXAMPLE II

In order to compare the binder-disintegrant properties of the precompacted-starch powders employed in the present invention with those of other compacted starches, the starting bleached native corn starch (Starch A) of Example I was converted to a precompacted-starch powder using Technique 3 of Example I with the exception that the moisture content of the starting starch was initially adjusted to about 18% by weight so that the starch was worked and modified to a lesser degree. The resultant compacted starch powder was characterized by a 2.9% cold-water solubles content, a swelling power of 3.0, a loose bulk density of 0.49 gm/ml., and flowability corresponding to an angle of repose of more than 40°.

The resultant compacted starch powder was tabletted alone using the procedure of Example I. The tablets obtained had an average hardness of 3 kg., a friability corresponding to an average weight loss of 1.93% and a disintegration time in water of 0.5–5 minutes. As evidenced by the poor flowability of the powder and the low hardness and high friability of the tablets prepared therefrom, the low cold-water solubles content powder is not suitable for use as a sole duel-functioning binder-disintegrant ingredient in preparing acceptable tablets by direct compression.

EXAMPLE III

This example illustrates the preparation of suitable tablet-binder disintegrant starches from oxidized corn starch and the use of the resultant binder-disintegrant starches in the preparation of tablets by direct compression.

Two samples of ground alkaline hypochlorite-oxidized corn starch (Starch B) were converted to compacted starch powder using Techniques 2 and 3 of Example I. However, in using Technique 2 the feed starch had a moisture content of 31.0% by weight and the roll temperature was maintained at 31° C. and in using Technique 3 the feed starch had moisture content of 27.1% by weight, the roll gap was 0.02 in., and the force feeder speed was 5 rpm. The properties of the resultant precompacted-starch powders (Starch $B_{DRM}$ and Starch $B_{A.C.}$, respectively) are set forth in Table 3 below. Using the procedure of Example I, tablets were formed from each of the precompacted-starch powders alone and formulations prepared by thoroughly mixing each powder separately with certain drugs and tabletting aids. The compositions of the tablets and their properties are shown in Table 4 below.

Table 3

| Example No. | Starch | Description | Starch Properties H$_2$O Content % | Starch Properties Cold Water Solubility, % | Starch Properties Swelling Power | Starch Properties Loose Bulk Density, gm/ml | Starch Properties Flowability angle of repose |
|---|---|---|---|---|---|---|---|
| III | B | Oxidized corn starch | 11.3 | 1.3 | 2.1 | — | — |
| | $B_{DRM}$ | Differential roll-milled Starch B | 11.7 | 10.2 | 3.6 | 0.56 | 34 |
| | $B_{A.C.}$ | Differential roll-milled Starch B | 12.3 | 33.6 | 7.1 | 0.63 | 27 |
| IV | C | Native corn starch | 11.1 | 0.3 | 1.9 | — | 36 |
| | $C_{DRM}$ | Differential roll-milled Starch C | 11.9 | 6.9 | 4.8 | 0.59 | 28 |
| V | D | Native high amylose starch | 10.9 | 0.4 | 2.6 | — | 29 |
| | $D_{DRM}$ | Differential roll-milled Starch D | 11.9 | 4.0 | 3.9 | 0.53 | 31 |
| VI | E | Acid-modified corn starch | 10.9 | 1.1 | 2.3 | — | 38 |

Table 3-continued

| Example No. | Starch | Description | Starch Properties | | | | |
|---|---|---|---|---|---|---|---|
| | | | $H_2O$ Content % | Cold Water Solubility, % | Swelling Power | Loose Bulk Density, gm/ml | Flowability angle of repose |
| | $E_{DRM}$ | Differential roll-milled Starch E | 12.0 | 17.7 | 4.0 | 0.63 | 31 |
| VII | F | Derivatized corn starch | 10.9 | 0.8 | 2.1 | — | 45 |
| | $F_{DRM}$ | Differential roll-milled Starch F | 12.1 | 31.5 | 6.5 | 0.63 | 34 |
| VIII | G | Cross-linked starch | 10.7 | 1.9 | 2.3 | — | 28 |
| | $G_{DRM}$ | Differential roll-milled Starch G | 11.9 | 21.1 | 7.0 | 0.60 | 29 |
| IX | H | Native potato starch | 13.9 | 0.6 | 2.2 | — | 31 |
| | $H_{DRM}$ | Differential roll-milled Starch H | 12.1 | 21.0 | 2.5 | 0.59 | 32 |

Table 4

| Example | Tablet No. | Starch Binder | Drug | Drug/Binder Weight Ratio* | % by wt. total Adjuvants, formula | | $H_2O$ Content % | Tablet Properties | | |
|---|---|---|---|---|---|---|---|---|---|---|
| | | | | | Talc | Colloidal Silica | | Average Hardness, kg. | Average Friability, % wt. loss | Disintegration time, min. |
| III | 18 | $B_{DRM}$ | — | 0:100 | — | — | 11.7 | 14.0 | 0.12 | 6.5–7.0 |
| | 19 | " | Phenacetin | 40:60 | — | 0.0103 | 7.4 | 5.4 | 0.43 | 3.5 |
| | 20 | " | Ascorbic Acid | 40:60 | 5.0 | 0.0055 | 7.0 | 5.0 | 0.16 | 3.0 |
| | 21 | " | NaPAS | 40:60 | 5.0 | 0.0078 | 12.8 | 8.4 | 0.34 | 45–60 |
| | 22 | " | APAP | 40:60 | 3.0 | 0.0108 | 7.7 | 7.8 | 0.18 | 3.5–4.0 |
| | 23 | $B_{A.C.}$ | — | 0:100 | — | — | 12.3 | 10.8 | 0.09 | 15.0 |
| | 24 | " | Phenacetin | 25:75 | — | 0.0118 | 8.3 | 4.6 | 0.41 | 5.0–6.0 |
| IV | 25 | $C_{DRM}$ | — | 0:100 | — | — | 11.9 | 14.3 | 0.10 | 5.0–6.5 |
| | 26 | " | Phenacetin | 40:60 | — | 0.0046 | 7.7 | 7.7 | 0.38 | 3.0–4.0 |
| | 27 | " | Ascorbic acid | 40:60 | 5.0 | 0.0093 | 7.1 | 6.0 | 0.31 | 5.5–6.0 |
| | 28 | " | NaPAS | 50:50 | 5.0 | 0.0094 | 13.3 | 6.7 | 0.28 | 70–80 |
| | 29 | " | APAP | 35:65 | 3.0 | 0.0094 | 7.7 | 8.4 | 0.14 | 3.5–4.0 |
| V | 30 | $D_{DRM}$ | — | 0:100 | — | — | 11.9 | 13.3 | 0.05 | 3.5–4.0 |
| | 31 | " | Phenacetin | 35:65 | — | 0.0138 | 7.9 | 7.1 | 0.34 | 2.5 |
| | 32 | " | Ascorbic acid | 45:55 | 6.0 | 0.0092 | 6.4 | 5.4 | 0.31 | 3.0–3.5 |
| | 33 | " | NaPAS | 50:50 | 5.0 | 0.0094 | 13.3 | 7.5 | 0.28 | 75–85 |
| | 34 | " | APAP | 35:65 | 3.0 | 0.0094 | 7.7 | 7.7 | 0.26 | 2.0–2.5 |
| VI | 35 | $E_{DRM}$ | — | 0:100 | — | — | 12.0 | 9.5 | 0.11 | 4.0 |
| VII | 36 | $F_{DRM}$ | — | 0:100 | — | — | 12.1 | 9.8 | 0.05 | 9.5–10.5 |
| VIII | 37 | $G_{DRM}$ | — | 0:100 | — | — | 11.9 | 9.5 | 0.11 | 4.0 |
| IX | 38 | $H_{DRM}$ | — | 0:100 | — | — | 12.1 | 10.1 | 0.12 | 29.0 |

*Based on binder dry substance weight

EXAMPLE IV

This example illustrates the preparation of a suitable tablet binder-disintegrant starch from native corn starch and the use of the resultant binder-disintegrant starch in making tablets.

Native corn starch (Starch C) was converted to a precompacted-starch powder using Technique 2 (differential roll-milling) of Example I except that a starch feed moisture content of 28.6% by weight and a roll temperature of 10° C. were employed. The properties of the starting starch and resultant precompacted-starch powder (Starch $C_{DRM}$) are set forth in Table 3. As in the procedure of the previous examples the precompacted-starch powder was tabletted alone, and was also mixed with various drugs and tabletting aids to provide formulations which were tabletted. The compositions and properties of the tablets obtained are shown in Table 4.

EXAMPLE V

This example illustrates the preparation of a tablet binder-disintegrant starch from a native high amylose starch and the use of the resultant binder-disintegrant starch in preparing tablets.

The procedure of Technique 2 (differential roll-milling) of Example I was employed to convert a native high amylose starch (commonly known as "Amylomaize" and designated Starch D) to a precompacted-starch powder except that a starch feed moisture content of 27.6% by weight and roll temperature of 10° C. were used. The properties of the starting starch and resultant precompacted-starch powder (Starch $D_{DRM}$) are set forth in Table 3. The properties of placebo and drug-containing tablets prepared using the precompacted-starch powder in the general tabletting procedure of Example I are shown in Table 4.

EXAMPLE VI

This example illustrates the preparation and use of a tablet binder-disintegrant starch derived from an acid-modified starch raw material.

An acid-modified starch (Starch E) having an alkali lfuidity of about 62 cc. (10 gm. starch, as is basis, 77° F. and 0.375 N sodium hydroxide) was converted to a precompacted-starch powder employing Technique 2 (differential roll-milling) of Example I except that the starch feed moisture content utilized was 28.0–30.5 by weight, the roll gap was 6 mils, and the roll temperature was maintained at 23°–26° C. A comparison of the properties of the starting granular starch and the resultant precompacted-starch powder (Starch $E_{DRM}$) obtained are set forth in Table 3. Following the tabletting procedure of Example I, placebo tablets (without drugs) were prepared using the precompacted-starch powder alone. The properties of the tablets obtained are reflected in Table 4.

The results of these tests indicate the resultant precompacted-starch powder is a suitable binder-disintegrant ingredient for use in preparing acceptable drug-containing tablets by direct compression as in the previous example.

EXAMPLE VII

This example illustrates the preparation and use of a tablet binder-disintegrant starch obtained from a derivatized granular starch raw material.

A granular derivatized corn starch containing about 2.5% acetyl groups (Starch F) was converted to a precompacted-starch powder using Technique 2 (differential roll-milling) of Example I except that the feed starch moisture content was 28.3–31% by weight, a roll gap of 12 mils was employed, and roll temperatures were maintained at 23°–24° C. The properties of the starting starch and the resultant precompacted-starch powder (Starch $F_{DRM}$) are set forth in Table 3. Using the tabletting procedure of Example I, placebo (drug-free) tablets were prepared from the precompacted-starch powders. The properties of the tablets are shown in Table 4.

When substituted as the binder-disintegrant ingredient in the preparation of the drug-containing tablets described in the preceding examples, the precompacted-starch powder provides tablets of properties comparable to those mentioned.

EXAMPLE VIII

This example illustrates the preparation and use of a tablet binder-disintegrant starch obtained from a cross-linked granular starch raw material.

The procedure of Example VI was repeated with the exception of substituting a granular cross-linked corn starch obtained by reacting oxidized corn starch with phosphorus oxychloride (Starch G) for the acid-modified starch. The properties of the starting starch and resultant precompacted-starch powder (Starch $G_{DRM}$) are set forth in Table 3. The characteristics of the tablets obtained are shown in Table 4. Drug-containing tablets prepared by direct compression, using the resultant precompacted-starch powder as a binder-disintegrant ingredient as in the preceding examples, have characteristics similar to such tablets described above.

EXAMPLE IX

This example illustrates the preparation and utilization of a tablet binder-disintegrant starch derived from potato starch.

The procedure of Example VII was repeated except that native potato starch (Starch H) was substituted for the derivatized corn starch. A comparison of the properties of the starting starch and the resultant precompacted-starch powder (Starch $H_{DRM}$) is shown in Table 3, and the characteristics of the placebo tablets prepared therefrom are listed in Table 4. When employed as a binder-disintegrant ingredient in preparing drug-containing compressed tablets, such as those prepared above by direct compression, the resultant precompacted-starch powder provides acceptable tablets.

EXAMPLE X

This example illustrates an embodiment of the present invention wherein a binder-disintegrant starch is employed in combination with an uncompacted starch in the preparation of active-ingredient tablets by direct compression, the uncompacted starch being employed as a filler and disintegrant ingredient in the tablets.

A sample of Starch $D_{DRM}$ (differential roll-milled native corn starch) described above in Example IV was thoroughly mixed with sodium p-aminosalicylate dihydrate (NaPAS) and ground bleached native corn starch containing about 10% by weight moisture in a weight ratio of drug; precompacted-starch; uncompacted starch: uncompacted starch of 30:60:10, starch dry substance basis. Talc and colloidal silica (Cab-o-sil) also were added during the mixing in amounts of 6.0% and 0.0109% by weight of the total formulation, respectively. The resultant powder which had a moisture content of 12.1% by weight was tabletted directly using the procedure of Example I. The resultant tablets were characterized by an average hardness of 8.7 kg., a friability corresponding to an average weight loss of 0.24%, and a disintegration time of 20–26 minutes.

EXAMPLE XI

This example illustrates embodiments of the present invention wherein a binder-disintegrant starch is employed in the preparation of tablets by direct compression wherein the tablets are intended for non-pharmaceutical uses.

Using Starch $A_p$ (pelletized bleached native corn starch) described in Example I as the binder-disintegrant ingredient and the tabletting procedure of Example I, tablets that disintegrate rapidly in water and have excellent hardness and friability properties are prepared from the following formulations:

| Plant Root-growth Stimulant Tablets | Parts by Weight |
|---|---|
| Starch $A_p$ | 90 |
| 1-Naphthalene acetic acid | 9 |
| Colloidal silica (Cab-o-Sil) | 1 |
| Garlic Tablets | |
| Starch $A_p$ | 23 |
| Powdered garlic (Dehydrated) | 70 |
| Colloidal silica (Cab-o-Sil) | 2 |

Table 5 below contains comparative data showing that compaction of starch so as to impart the properties set forth above in table form on page 8 renders the starch powder useful in forming tablets by direct compression whereas the same starch, non-compacted, does not have this property. In the table the heading "Allis-Chalmers Compacter Conditions" refers to Technique 3 set forth on page 30 above while the heading "Differential Roll Mill Conditions" refers to Technique 2 set forth above on pages 29 and 30. The starch used in Samples Nos. 1–10, 12 and 13 is ordinary powder native corn starch bleached with sodium hypochlorite to make it whiter while the oxidized starch used in Sample 11 is a corn starch oxidized by sodium hypochlorite under alkaline conditions until it has about 0.5% carboxyl groups.

The data in Table 5 may be summarized as follows:

(a) Samples 1, 2, 7, 8, 9 and 10, which were not compacted and which did not fall within the parameters set forth on page 8 with respect to at least two of cold water solubility, swelling power, loose bulk density, and moisture content, could not be tabletted.

(b) Samples 3, 4, 5, 6, 11, 12 and 13, which were precompacted, could be tabletted. However, sample 3 had a cold water solubility below the required minimum and the tablets formed therefrom were not satisfactory since they were not sufficiently hard and were excessively friable. Samples 4, 5 and 6 had values for cold water solubility, loose bulk density and swelling power within the range as set forth in the table on page 7.

(c) Sample 13, which was compacted well beyond any of the others, had excess cold water solubility and excess swelling power. While it could be tabletted, the tablets did not disintegrate in over 45 minutes, well beyond the requirements for a useful tablet-binder-disintegrant.

(d) In the Allis-Chalmers Compactor, increasing compaction is obtained by narrowing the gap, increasing the water content, increasing the speed of the feeder, increasing the bearing pressure or any combination of these. The data for Samples 3, 4, 5, and 6 show that increasing the extent of compaction increased the tablet hardness and disintegration time while decreasing friability.

starch which was 100% cold water soluble, blended with an equal one part of regular granular cornstarch with 0.125% added oil. About 62% by weight of the particles were −270 mesh. The above Kessinger composition (designated Sample A) was compared to a precompacted-starch powder made according to the present invention (designated Sample B). Sample B of the invention was obtained by first precompacting cornstarch at a moisture content in the range of 16–19% in a Sprout-Waldron pellet mill with no supplementary thermal energy. All of Sample B was subjected to the precompaction. The resulting precompacted-starch was dried to a moisture content of about 12.3%, and ground and screened. The resulting Sample B precompacted-starch powder was free-flowing, has a loose bulk density of 0.61 g/ml., cold water solubility 14.3%, a swelling power of 4.4, a moisture content of 12.3%, and when viewed microscopically, the Sample B product was observed to include both birefringent granules and non-birefringent fragments of granules. The particle size distribution of Sample B was:

| | |
|---|---|
| +40 mesh particles | none |
| −80 mesh | 98% |
| +270 mesh | 34% |
| −270 mesh | 64% |

Attempts were made to tablet Sample A Kessinger

Table 5

| Sample No. | Type of Starch | Allis Chalmers Compacter Conditions | | | | Powder Subjected to Tabletting (<80 mesh) | | | | Tablet | | |
|---|---|---|---|---|---|---|---|---|---|---|---|---|
| | | $H_2O$ In Feed Starch | Roll Gap (Inches) | Force Feeder (RPM) | Bearing Pressure (Lbs.) | % Cold Water Solubles | Loose Bulk Density gm/ml. | Swelling Power | % $H_2O$ | Hardness (kg) | Friability % wt. Loss | Disintegration (min.) |
| 1 | Bleached Starch | 10.0 | — | — | — | 0.3 | 0.52 | 1.9 | 10.0 | (Unable | | |
| 2 | Bleached Starch | 20.7 | — | — | — | 0.8 | 0.46 | 2.45 | 9.7 | | To Make | Tablets) |
| 3 | Bleached Starch | 18.2 | 0.05 | 5 | 1000 | 2.9 | 0.49 | 2.97 | 11.9 | 3.0 | 1.93 | 0.5–1.5 |
| 4 | Bleached Starch | 18.2 | 0.05 | 16 | 1300 | 7.4 | 0.50 | 5.02 | 11.9 | 7.3 | 0.32 | 5.0–5.5 |
| 5 | Bleached Starch | 21.6 | 0.05 | 15 | 1000 | 11.6 | 0.59 | 7.17 | 11.9 | 14.7 | 0.10 | 9.0–9.5 |
| 6 | Bleached Starch | 21.6 | 0.02 | 10 | 1000 | 13.3 | 0.55 | 9.04 | 11.9 | 12.2 | 0.05 | 18.0–19.5 |
| 7 | Bleached Starch | 11.6 | — | — | — | 0.4 | 0.51 | 2.01 | 11.6 | (Unable | | |
| 8 | Bleached Starch | 9.1 | — | — | — | 0.4 | 0.45 | 2.23 | 9.1 | | To | |
| 9 | Bleached Starch | 10.4 | — | — | — | 0.2 | 0.56 | 1.97 | 10.4 | | Make | Tablets) |
| 10 | Bleached Starch | 7.4 | — | — | — | 1.3 | 0.44 | 2.06 | 7.4 | | | |
| | | Differential Roll Mill Conditions | | | | | | | | | | |
| | | Roll Gap (Mils) | Roll Speeds/Ft/min | No. of Passes | | | | | | | | |
| 11 | Oxidized Starch | 31.0 | 12 | 50 and 70 | 2 | 10.2 | 0.56 | 3.64 | 11.7 | 14.0 | 0.12 | 6.5–7.0 |
| 12 | Bleached Starch | 25.2 | 12 | 50 and 70 | 4 | 13.1 | 0.60 | 6.79 | 11.8 | 13.2 | 0.13 | 7.5–8.5 |
| 13 | Bleached Starch | 27.0 | 12 | 50 and 70 | 4 minutes* | 61.1 | 0.56 | 12.3 | 11.8 | 14.8 | 0.01 | >45** |

*Equivalent to 128 to 180 passes.
**Had not disintegrated in 45 minutes when test was halted

EXAMPLE XII

To demonstrate the difference in behavior of the cold water soluble starch blended with a granular starch described in Kessinger (U.S. Pat. No. 3,171,747) from the precompacted-starch powder of the subject invention, the two materials were directly compared as direct compression tabletting vehicles. The Kessinger composition employed comprised one part extruded cornstarch composition in a direct compression tabletting machine. The Sample A material did flow well enough to fill the die of the tabletting machine, and even when the tabletting was operated at the greatest possible compression with manual loading it was not possible to produce a hard, non-friable tablet. Only underweight tablets could be produced using the Sample A Kessinger composition. Such tablets which could be produced from the Sample A composition were compared to tablets made with the Sample B precompacted-starch powder of the subject invention and using only normal compression on the same tabletting machine. The comparisons observed are set forth below in Table 6:

Table 6

| TEST: | Sample A Kessinger Composition | Sample B precompacted-starch powder |
|---|---|---|
| Friability: | 100% | 0.07% |
| Strong-Cable Hardness | 0.2 kg (see test procedure) | 14.9 kg (see test procedure) |
| Disintegration: | Did not dissolve, even after 3600 seconds, became gummy mass, dry on inside of tablet | Complete disintegration within 470 seconds. |

The above data shows that the Sample A Kessinger baker's dusting composition, which is a blend of two starches, is not useful as a direct compression tabletting vehicle, whereas the precompacted-starch powder of the subject invention, which is not a blend, in most suited for use as a direct compression tabletting vehicle, and is capable of forming hard, substantially non-friable tablets which disintegrate effectively to release the active ingredient.

EXAMPLE XIII

To show that even a larger percentage of granular cornstarch did not improve the properties of the Kessinger composition for tabletting, another blend (designated Sample C) following Kessinger's disclosures was made up as follows:

One part of extruded corn starch (66% cold water soluble was blended with:
two parts of non-extruded starch; and 0.25% added oil.

The particle size of the product was all −40 mesh size and about 60% by weight was −270 mesh size, and the resulting final blend had a cold water solubility of about 33% by weight. Attempts to tablet using the above Sample C composition are set forth below:

Table 7

| TEST: | SAMPLE C | SAMPLE B |
|---|---|---|
| Friability | 100% | 0.07% |
| S.C. hardness | 0.4 kg | 14.9 kg |
| Disintegration | 1800-2400 seconds from a soft, friable tablet. | 465 seconds, from a hard, non-friable tablet |

The Sample C blend could only be tabletted by loading the tabletting machine manually because the blend did not exhibit good flow properties. The soft, friable tablets made from the Sample C blend were underweight, and could not be handled in the normally required manner because of their excessive friability. Normal handling requires a tablet hardness of at least about 4 kg.

The above comparisons demonstrate that blends of a physically extruded starch with a non-extruded granular starch such as disclosed in Kessinger do not provide a functional direct compression tabletting vehicle. The untreated portion of the blended product has not been subjected to the physical working, and appears to interfere with successful tabletting. Presence of about fifty percent of an extruded starch also interferes with the disintegration of any underweight tablets which can be made according to the disclosure of Kessinger U.S. Pat. No. 3,171,747. This result is not surprising, because the Kessinger disclosure is directed to a baker's dusting composition which is intended for an entirely different purpose.

The direct compression tabletting vehicle of the subject invention, in contrast, may be characterized as an unusually mobile, free-flowing precompacted-starch powder, capable of being tabletted into hard, non-friable full-weight tablets by direct compression tabletting. The resulting tablets disintegrate effectively to release the active ingredient; the direct compression tabletting vehicle of the invention can serve both as a binder and a disintegrant. In addition, the free-flowing and disintegrant properties of this starch product have readily suited it for use as a blending agent-filler for dissolvable capsules (e.g., gelatin capsules) containing active ingredients in powder form.

All portions of the precompacted-starch powder of this invention have been subjected to a precompaction without added thermal energy, and the resulting product is a synergistic and integral whole which has a portion of birefringent granules which aid tablet disintegration, and compatible, non-birefringent fragments of granules which aid in binding the tablet but do not interfere with tablet disintegration as was the case with the Kessinger blend described above. In addition, the combination of precompaction with no added thermal energy, and grinding to obtain a certain particle size distribution makes other costly blending or pregranulation steps unnecessary for most direct compression tabletting uses.

Other patentees, even more recent than the subject invention, have described more complex direct compression tabletting vehicles which are more costly to prepare and blend, and which require a pregranulation process in some cases. The direct compression tabletting vehicle of the subject invention is a direct and deceptively simple solution to the problems of direct compression tabletting, and satisfies in one material the tabletting requirements of compatibility, flowability, density, hardness and binding ability, and also the tablet functional requirements of active ingredient release (disintegratability) and it is an inert, non-toxic substance which may be ingested without adverse reactions.

The invention has been described above as completely as possible with specific examples, but further variations, adaptations, uses and departures as come within the known or customary practice of the art, and utilizing the essential features of the invention are intended to be included in the scope of the claims set forth below:

We claim:

1. A directly compressible tabletting vehicle having binder-disintegrant properties consisting essentially of a free-flowing, precompacted-starch powder derived from a cold water insoluble granular starch which has been subjected to physical compaction without supplementary thermal energy to obtain a precompacted-starch powder having birefringent granules, non-birefringent granules and non-birefringent fragments of granules in which some aggregates of birefringent and non-birefringent granules and fragments are present, and having a loose bulk density in the range of from about 0.5 to about 0.7 grams per milliliter, a moisture content in the range of from about 9 to about 16%, total weight basis, said precompacted-starch powder being pulverized and screened to obtain a particle size distribution which is free of +40 mesh particles and at least 90% of said precompacted-starch powder is −80 mesh size, at least about 10% is +270 mesh size, and from about 30% to about 90% is −270 mesh size, on a total weight basis, said precompacted-starch powder having a cold water solubility of from 4% to about 40% by weight, and further characterized as capable of being directly compressed into a carrier tablet containing active ingredients, said tablet having a hardness index of at least about 4 kg., a friability weight loss of less than about 1.0%, a swelling power of 2.5 to about 12, and said tablet being capable of effectively disintegrating when placed in water.

2. The tabletting vehicle of claim 1, in which the cold water solubility of the precompacted-starch powder is in the range of 10–20% by weight.

3. The tabletting vehicle of claim 1, in which the precompacted-starch powder is cornstarch.

4. The tabletting vehicle of claim 3, further characterized by being capable of being formed by direct compression at a pressure as low as about 2000 pounds into hard, substantially non-friable tablets having a hardness value of at least about 8 kg.

5. The tabletting vehicle of claim 4, in admixture with up to about 80% by weight, based on the weight of said vehicle, of at least one active ingredient.

6. A method for preparing tablets comprising forming an admixture of the product of claim 5, and directly compressing the mixture into tablets.

7. A method of producing a direct compression vehicle for tabletting comprising:
  a. precompacting a cold water insoluble granular cornstarch at a temperature below its gelatinization temperature and with no added thermal energy, the precompacting means being selected from the group consisting of differential roll mill, concurrent roll mill, pellet mill, and wet extrusion apparatus, said granular cornstarch having a moisture content in the range of 14 to 40% by weight:
  b. grinding the resulting precompacted starch to obtain a free-flowing precompacted-starch powder direct compression vehicle for tabletting comprising birefringent starch granules, non-birefringent starch granules, and fragments thereof both in discrete and aggregated particle form, said powder mixture having a cold water solubility from 6–20% based on the dry substance, a swelling power from 3.5 to 10, a loose bulk density of 0.50 to 0.70 grams per milliliter, and further characterized in that tablets made solely from said vehicle having a hardness index of at least 8 kilograms, a friability of less than 0.5% based on weight loss, and a disintegration time in water of fifteen minutes or less.

8. A direct compression vehicle having both binder and disintegrant properties consisting essentially of a compacted-starch powder having a cold-water solubility in the range of from about 4% to about 20% by weight, dry substance basis, and a swelling power in the range of from about 2.5 to about 12, said powder being superficially dry and free-flowing and having birefringent and non-birefringent granules, and non-birefringent fragments of granules, including some aggregates of birefringent granules and non-birefringent fragments, said powder having a loose bulk density in the range of from about 0.5 to about 0.7 grams per milliliter and a moisture content in the range of from about 9 to about 16%, total weight basis, said powder having a particle size distribution essentially free of +40 mesh material and on a total weight basis, at least 90% of said powder is −80 mesh size, at least about 10% is +270 mesh size, and from about 30% to about 90% is −270 mesh size, and further characterized in that said compacted-starch powder is directly compressible into a carrier tablet containing active ingredients and having a hardness index of at least about 4 kg., a friability weight loss of less than about 1.0%, and said tablet being capable of effectively disintegrating when placed in water.

9. The compacted-starch powder direct compression tabletting vehicle of claim 8, in which the starch is cornstarch and in which the carrier tablet is capable of effectively disintegrating in water in less than about 1800 seconds.

10. A direct compression tabletting vehicle consisting essentially of a free-flowing precompacted-starch material having a cold-water solubility in the range from 4% to 20% by weight, dry substance basis, a swelling power of 2.5 to 12 and comprising birefringent and non-birefringent starch granules, non-birefringent starch granule fragments, and aggregates of birefringent starch granules with non-birefringent starch granule fragments, said powder having a loose bulk density in the range of 0.5 to 0.7 gram per milliliter and a moisture content in the range of from 9 to 16%, total weight basis, and having a particle size distribution essentially free of +40 mesh particles, at least 90% of the total weight of said mixture are particles which pass through an 80 mesh screen, about 10% are particles which will not pass through a 270 mesh screen, and 30% to 90% are particles which will pass through a 270 mesh screen, said tabletting powder being directly compressible without pregranulation into dense, nonfriable tablets having a hardness of at least 5000 grams which disintegrate effectively when placed in water.

11. A direct compression tabletting vehicle consisting essentially of precompacted-starch powder for making carrier tablets for active ingredients consisting of a free-flowing powder containing birefringent starch granules, non-birefringent starch granules, and fragments thereof both in discrete and aggregated particle form, said powder having a particle size distribution such that at least about 10% is +270 mesh size, and about 30% to 90% is −270 mesh size, on a total weight basis, said powder having a cold water solubility from 6–20% based on the dry substance, a swelling power from 3.5 to 10, a loose bulk density of 0.55 to 0.70 grams per milliliter, and tablets made solely from said powder having a hardness index of at least 8 kilograms, a friability of less than 0.5% based on weight loss, and a disintegration time in water of fifteen minutes or less.

* * * * *

UNITED STATES PATENT AND TRADEMARK OFFICE
CERTIFICATE OF CORRECTION

PATENT NO. : 4,072,535
DATED : February 7, 1978
INVENTOR(S) : Rolland W. P. Short; Frank Verbanac It is certified that error appears in the above-identified patent and that said Letters Patent are hereby corrected as shown below:

Column 5, line 64, for "54:2314f" read ---54:23184f---
Column 5, line 68, for "may be" read ---made by---
Column 9, line 60, for "0155-0170" read ---0.55-0.70---
Column 13, line 37, for "The pressure of" read ---The presence of---
Column 13, line 41, for "of 31 270 mesh." read ---of -270 mesh.---
Column 17, line 2, for "Series (CM" read ---Series CM---
Column 17, line 36, for "25-2%" read ---25.2%---
Column 18, line 39, for "Rable 2" read ---Table 2---
Column 18, line 43, for "fourpunch" read ---four-punch---
Column 20, line 18, for "0.5-5" read ---0.5-1.5---
Column 22, line 67, for "lfuidity" read ---fluidity---
Column 23, line 3, for "28.0-30.5" read ---28.0-30.5%---
Column 24, line 20, "precompacted-starch;uncompacted starch:uncompacted starch of 30:60:10," read ---precompacted-starch:uncompacted starch of 30:60:10,---
Column 27, Table 6, Column entitled TEST: for "Strong-Cable" read ---Strong-Cobb---
Column 29, line 60, for "compression vehicle" read ---compression tabletting vehicle---
Column 30, line 45, "hardness of" read ---hardness index of---.

Signed and Sealed this

Twentieth Day of June 1978

[SEAL]

Attest:

RUTH C. MASON
Attesting Officer

DONALD W. BANNER
Commissioner of Patents and Trademarks